United States Patent [19]
Berry et al.

[11] Patent Number: 5,948,894
[45] Date of Patent: Sep. 7, 1999

[54] IMMUNOADSORBENT REAGENTS

[75] Inventors: Mark J Berry, Wellingborough; Paul J Davis, Felmersham; Martine E Verhoeyen, Rushden; Ronald F. J. De Winter, Bedford, all of United Kingdom

[73] Assignee: Unilever Patent Holdings B.V., Rotterdam, Netherlands

[21] Appl. No.: 08/475,081

[22] Filed: Jun. 7, 1995

Related U.S. Application Data

[63] Continuation of application No. 08/310,103, Sep. 21, 1994, abandoned, which is a continuation of application No. 08/112,056, Aug. 26, 1993, abandoned, which is a continuation of application No. 07/979,448, Nov. 20, 1992, abandoned, which is a continuation of application No. 07/628,910, Dec. 18, 1990, abandoned.

[30] Foreign Application Priority Data

Dec. 18, 1989 [GB] United Kingdom .................... 8928501

[51] Int. Cl.⁶ ........................ G01N 33/543; C07K 16/00; C07K 17/02; C07K 17/14
[52] U.S. Cl. ........................ 530/391.1; 435/7.1; 436/518; 436/527
[58] Field of Search .......................... 530/391.1; 435/7.1; 436/518, 527

[56] References Cited

U.S. PATENT DOCUMENTS 4,863,869  9/1989  Balint .
5,041,381  8/1991  Abrams et al. .

FOREIGN PATENT DOCUMENTS 0290406   2/1988   European Pat. Off. .
368684    5/1990   European Pat. Off. .
3627063   2/1988   Germany .
8809344   12/1988  WIPO .
8909088   10/1989  WIPO .

OTHER PUBLICATIONS

Ward et al. (1989) *Nature*, vol. 341, 544–546.
Hayashi et al. (1989) *Chromatographia*, vol. 27, 569–573.
Klausner (2986) *Bio/Technology*, vol. 4, 1041–1043.
Dierks et al. (1986) *Molecular Immunology*, vol. 23, 403–411.
Hollander et al. (1986) *Molecular Immunology*, vol. 23, 927–933.
Berry et al. (1991) *J. Chromatography*, vol. 587, 161–169.
Bird et al. (1988) *Science*, vol. 242, 423–426.
Zopf et al. (1990) *Nature*, vol. 346, 87–88.
Hochman et al. (1973) *Biochemistry*, vol. 12, 1130–135.
Affinity Chromatography, Pharmaia, 1979 pp. 92–95.

*Primary Examiner*—Toni R. Scheiner
*Assistant Examiner*—Nancy A. Johnson
*Attorney, Agent, or Firm*—Pillsbury Madison & Sutro LLP

[57] ABSTRACT

Improved affinity purification media are provided by the use of small specific binding agents, especially Fv antibody fragments or single domain antibody fragments, immobilised on porous carriers having pore sizes in the range 30–1000 angstroms, preferably 30–300 angstroms. Silica is a preferred carrier. The small fragments are able to penetrate the pores and maximise the effective surface area of the carrier, and the microporous silica is sufficiently robust to be used at high pressure, so enabling the speed and/or throughput of a purification procedure to be increased.

13 Claims, 7 Drawing Sheets

Fig. 1a

```
                homology        Kpn1                                      EcoR1
5' TAG CCC TTA TTA CAG GTA CCC CTT ACC GGA ATT CCC (GCT ACC)n
   BamH1     homology
   GGA TCC TGA GGA GAC GGT 3'                              n=0-5
```

Fig. 1b

```
       homology             Kpn1
5' TAG CCC TTA TTA CTT CAG GTA CCC CTT ACC GGA GTT CCC (GCT ACC)n
   Bam HI    homology
   GGA TCC TGA GGA GAC GGT 3'                              n = 0-5
```

Fig. 1c

```
       homology             Kpn1                                    Sac II
5' TAG CCC TTA TTA GGG TAC CAA AAG CTT CGC (AAG TGC)n  TAC CGC GGC
   homology
   TGA GGA GAC GGT 3'                                      n = 0-5
```

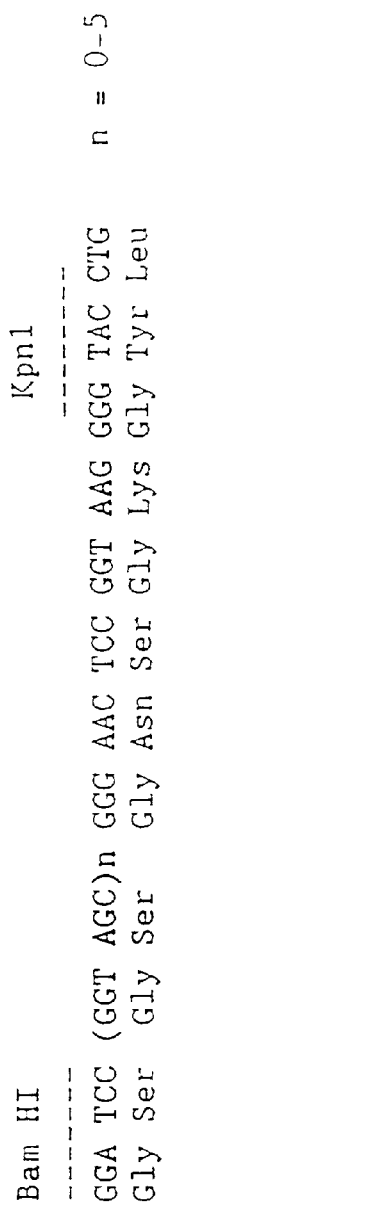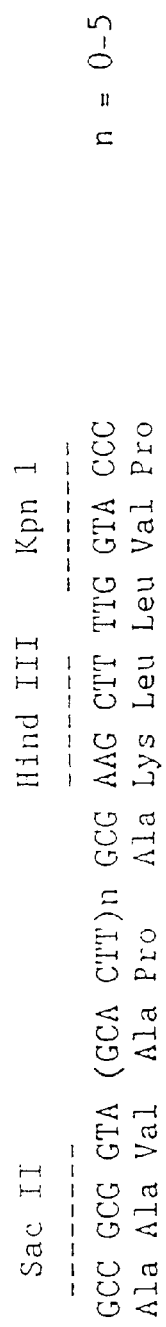
Fig. 2a
hydrophylic tail
Bam HI                                                    Kpn1
GGA TCC (GGT AGC)n GGG AAC TCC GGT AAG GGG TAC CTG         n = 0-5
Gly Ser  Gly Ser   Gly Asn Ser Gly Lys Gly  Tyr Leu
Fig. 2b
hydrophobic tail
Sac II                         Hind III   Kpn 1
GCC GCG GTA (GCA CTT)n GCG AAG CTT TTG GTA CCC              n = 0-5
Ala Ala Val  Ala Pro   Ala Lys Leu Leu Val Pro

5,948,894

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
        (A) LENGTH: 11 amino acids
        (B) TYPE: amino acid
        (D) TOPOLOGY: linear (xi) SEQUENCE DESCRIPTION: SEQ ID NO:1:

```
Glu Gln Lys Leu Ile Ser Glu Glu Asp Leu Asn
1               5                   10
```

(2) INFORMATION FOR SEQ ID NO:2:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ix) FEATURE:
        (A) NAME/KEY: misc_difference
        (B) LOCATION: replace(37..42, "")
        (D) OTHER INFORMATION: /note= "nnn nnn represents (GCT
           ACC)n where n=0 to 5"

(xi) SEQUENCE DESCRIPTION: SEQ ID NO:2:

```
TAGCCCTTAT TACAGGTACC CCTTACCGGA ATTCCCNNNN NNGGATCCTG AGGAGACGGT        60
```

(2) INFORMATION FOR SEQ ID NO:3:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ix) FEATURE:
             (A) NAME/KEY: misc_difference
             (B) LOCATION: replace(40..45, "")
             (D) OTHER INFORMATION: /note= "nnn nnn represents (GCT
                 ACC)n where n=0 to 5"

(xi) SEQUENCE DESCRIPTION: SEQ ID NO:3:

TAGCCCTTAT TACTTCAGGT ACCCCTTACC GGAGTTCCCN NNNNNGGATC CTGAGGAGAC      60

GGT                                                                   63

(2) INFORMATION FOR SEQ ID NO:4:

(i) SEQUENCE CHARACTERISTICS:
             (A) LENGTH: 57 base pairs
             (B) TYPE: nucleic acid
             (C) STRANDEDNESS: single
             (D) TOPOLOGY: linear (ix) FEATURE:
             (A) NAME/KEY: misc_difference
             (B) LOCATION: replace(31..36, "")
             (D) OTHER INFORMATION: /note= "nnn nnn represents (AAG
                 TGC)n where n=0 to 5"

(xi) SEQUENCE DESCRIPTION: SEQ ID NO:4:

TAGCCCTTAT TAGGGTACCA AAAGCTTCGC NNNNNNTACC GCGGCTGAGG AGACGGT         57

(2) INFORMATION FOR SEQ ID NO:5:

(i) SEQUENCE CHARACTERISTICS:
             (A) LENGTH: 36 base pairs
             (B) TYPE: nucleic acid
             (C) STRANDEDNESS: single
             (D) TOPOLOGY: linear (ix) FEATURE:
             (A) NAME/KEY: CDS
             (B) LOCATION: 1..36

(ix) FEATURE:
             (A) NAME/KEY: misc_difference
             (B) LOCATION: replace(7..12, "")
             (D) OTHER INFORMATION: /note= "nnn nnn represents (GGT
                 AGC)n where n=0 to 5"

(xi) SEQUENCE DESCRIPTION: SEQ ID NO:5:

GGATCCNNNN NNGGGAACTC CGGTAAGGGG TACCTG                                36

(2) INFORMATION FOR SEQ ID NO:6:

(i) SEQUENCE CHARACTERISTICS:
             (A) LENGTH: 12 amino acids
             (B) TYPE: amino acid
             (D) TOPOLOGY: linear (ix) FEATURE:
             (A) NAME/KEY: Modified-site
             (B) LOCATION: 3..4
             (D) OTHER INFORMATION: /note= "Xaa Xaa represents (Gly
                 Ser)n where n=0 to 5"

(xi) SEQUENCE DESCRIPTION: SEQ ID NO:6:

Gly Ser Xaa Xaa Gly Asn Ser Gly Lys Gly Tyr Leu
1               5                   10

(2) INFORMATION FOR SEQ ID NO:7:

(i) SEQUENCE CHARACTERISTICS:
             (A) LENGTH: 33 base pairs
             (B) TYPE: nucleic acid
             (C) STRANDEDNESS: single

```
        (D) TOPOLOGY: linear (ix) FEATURE:
         (A) NAME/KEY: CDS
         (B) LOCATION: 1..33

(ix) FEATURE:
         (A) NAME/KEY: misc_difference
         (B) LOCATION: replace(10..15, "")
         (D) OTHER INFORMATION: /note= "nnn nnn represents (GCA
             CTT)n where n=0 to 5"

(xi) SEQUENCE DESCRIPTION: SEQ ID NO:7:

GCCGCGGTAN NNNNNGCGAA GCTTTTGGTA CCC                                 33

(2) INFORMATION FOR SEQ ID NO:8:

(i) SEQUENCE CHARACTERISTICS:
         (A) LENGTH: 11 amino acids
         (B) TYPE: amino acid
         (D) TOPOLOGY: linear (ix) FEATURE:
         (A) NAME/KEY: Modified-site
         (B) LOCATION: 4..5
         (D) OTHER INFORMATION: /note= "Xaa Xaa represents (Ala
             Pro)n where n=0 to 5"

(xi) SEQUENCE DESCRIPTION: SEQ ID NO:8:

Ala Ala Val Xaa Xaa Ala Lys Leu Leu Val Pro
1               5                   10
```

IMMUNOADSORBENT REAGENTS

This is a continuation of application Ser. No. 08/310,103, filed on Sep. 21, 1994, which was abandoned upon the filing hereof which was a CON of 08/112,056, filed Aug. 26, 1993, now abandoned, which was a CON of 07/979,448, filed Nov. 20, 1992, now abandoned, which was a CON of 07/628,910, filed Dec. 18, 1990, now abandoned.

FIELD OF THE INVENTION

This invention relates to reagents having specific binding properties, and particularly to their use in immuno adsorption processes, especially immunoaffinity purification processes.

BACKGROUND OF THE INVENTION

Natural antibodies, either polyclonal or monoclonal, have been used as specific binding reagents for a considerable time. When immobilised on solid phases they can be used in purification procedures.

Antibodies are large complex multi-chain proteinaceous structures. Although it has been appreciated for some while that substantial portions of these structures seem unrelated to the specific binding properties of the antibodies, the minimum portion necessary to provide adequate specific binding has been a matter of debate. It has already been shown that so-called Fv fragments, ie. an antibody fragment essentially comprising only a single heavy-chain variable region and its corresponding light chain variable region, can exhibit specific binding activity. Very recently it has also been shown by Ward et al (*Nature*, 1989, Vol. 341, p544–546) that a single variable domain from an antibody ("Dab") can exhibit significant specific binding activity. The production of single variable domain antibodies (Dabs), as described by Ward et al, is also described in detail in EP 0368684 A1 (Medical Research Council) published on May 16, 1990. There is now some evidence that peptides much shorter than the Dab, so-called paralogs, can be designed to mimic antibody binding to some extent (Kauva et al, *Biochromatography*, 5, 1990, p22).

To be of practical use in immunoadsorption processes, specific binding activity alone is not sufficient. The specific binding agent must also be capable of being linked to a solid phase such as a carrier material in a column. Ideally, this linkage is achievable without any significant adverse affect on the specific binding activity. Such adverse affects can easily arise through chemical or conformational changes in the specific binding region, or simply by physical (steric) hindrance of access to the specific binding region. In the case of conventional specific binding reagents, particularly whole antibody molecules or large portions of such molecules such as Fab fragments, the specific binding region or regions comprise only a minor proportion of the total molecule. The comparatively vast residual bulk of the molecule, which is apparently not directly involved in the specific binding activity, provides abundant scope for the existence of locations which can participate in chemical or physical linkage to solid phases. These regions can be relatively remote from the essential specific binding regions, such that the resulting linkages need not interfere with the specific binding activity.

However, in the case of a specific binding entity essentially comprising only one or more variable domains unassociated with any substantial portion of the originating antibody or antibodies, eg. a Fv fragment or a single variable domain, the relative proportion of the molecule which participates in the essential specific binding activity is very much higher. Indeed, it might be expected that any attempt to link the small specific binding entity to a solid phase would entail a very high risk that the essential specific binding activity will be adversely affected.

SUMMARY OF THE INVENTION

In contrast, we have surprisingly found that it is possible to immobilise small specific binding agents on porous carrier materials. Indeed, not merely is this possible, but the resulting immunoadsorbent can have enhanced properties, particularly because the use of the small specific binding agent permits advantage to be taken of improved carrier materials. By means of the invention, it is possible to change immunoaffinity from a bench-scale laboratory technique into a technique that can be applied economically and efficiently on a scale appropriate for industrial recovery or purification of a wide range of commercially important materials.

An embodiment of the invention is an immunoadsorbent material comprising a specific binding agent having a molecular weight of not more than about 25,000, immobilised on a porous solid phase carrier material.

The invention particularly provides an immunoadsorbent material comprising a specific binding agent immobilised on a porous solid phase carrier material, wherein the specific binding agent comprises one or more variable domain proteins (VH and/or VL) unassociated with any substantial portion of originating antibody or antibodies. The specific binding agent can be a single variable domain protein (Dab), or a combination of variable domains, especially an Fv fragment. Fv fragments may be either 'natural' Fvs (where the $V_H$ and $V_L$ are held together by hydrophobic forces) or 'single-chain' Fvs (where the $V_H$ and $V_L$ are linked by a short peptide).

PREFERRED EMBODIMENTS OF THE INVENTION

Conventional porous solid phase carrier materials can be used, such as agarose; polystyrene; controlled pore glass (CPG); celluloses; dextrans; agarose-filled kieselguhr; and synthetic polymers and co-polymers such as the hydrophylic "Pw" polymers manufactured by Tosoh, polytetrafluoroethylene (PTFE) that has been rendered hydrophylic, polymers of N-acryloyl-2-amino-2-hydroxymethyl-1,3-propane diol (optionally with other monomers), and co-polymers of 2-hydroxy methacrylate with ethylene dimethacrylate (HEMA). A particularly preferred carrier material is porous amorphous silica. These carrier materials may be particulate (eg. beads or granules, generally used in extraction columns), or in sheet form, eg. membranes or filters, which can be flat, pleated, or hollow fibres or tubes.

Relatively incompressible carriers are preferred, especially silica. These have important advantages for use in industrial-scale chromatography because they can be packed in columns operable at substantially higher pressure than can be applied to softer carrier materials such as agarose. Moreover, silica, glass and synthetic polymers and copolymers such as "PW" polymers possess particularly appropriate densities for use in stirred tanks and fluidised beds. These media are also preferred for high speed analytical separation.

An important embodiment of the invention is an immunoadsorbent material comprising a specific binding agent immobilised on porous silica or the like, the specific binding agent comprising one or more variable domain proteins unassociated with any substantial portion of originating antibody or antibodies.

A particularly important embodiment of the invention is an immunoadsorbent material comprising a specific binding agent immobilised on a porous carrier material, such as silica, having a pore size of at least 30A but not greater than 1000A, wherein the specific binding agent comprises one or more variable domain proteins unassociated with any substantial portion of originating antibody or antibodies. Preferably, the carrier has a pore size of at least 60A. Preferably, the pore size is not greater than 500A, and more preferably not greater than 300A.

Another important aspect of the invention is the use of an immunoadsorbent material comprising an Fv or Dab fragment, on a porous carrier material selected from the group consisting of amorphous silica, controlled pore glass, and synthetic polymers and copolymers, wherein the carrier material has a nominal pore size in the range 30–300A, to enhance the speed and/or throughput of an affinity purification process.

For convenience, the invention will be particularly described in relation to the use of silica as the carrier material. The reader will appreciate, however, that the invention encompasses the use of other porous carrier materials having properties analogous to those of silica.

Chromatographic silicas generally have a nominal pore size in the range of 30–300 angstroms (A). Silicas with pore sizes of 200–300A are available commercially, and recommended as wide-pore solid phases for use in traditional physical protein separations. These silicas may be derivatised with ligands to make functional high performance liquid chromatography (HPLC) media, such as anion-exchangers.

Silicas having pore sizes of 200–300A are still robust, and columns packed with such material can be operated at high pressure. However, such silicas are quite unsuitable as carriers for conventional immunoreagents (ie. whole antibody molecules or large antibody fragments such as Fab fragments) because although such large molecules may fit into the pores in the silica, the resulting immunoabsorbent material would be very inefficient because there would be much less room left within the pores for any antigen to enter and engage with the specific binding agent. (Mohan et al, in *Separations for Biotechnology*, ed. D L Pyle, 1990). If intact antibodies are used as an immunoadsorbent material on a silica support, the pore size of the silica needs to be substantially larger eg. in excess of 1000A. Silicas with a pore-size of 1000A have three disadvantages: they are more expensive to manufacture; they are less robust; and they have a lower surface area per unit volume (which in turn restricts the amount of ligand which can be immobilised). See Ritchie et al, *Chromatograhy and Analysis*, 1990.

Pore size determination

The nominal pore size of a carrier medium, such as amorphous silica, is often referred to in the art as the mean pore diameter, and expressed as a function of pore volume and surface area. In principle, pore volume and surface area can be determined by standard nitrogen absorption methods of Brunauer, Emmett and Teller (BET). The mean pore diameter is calculated from the Wheeler equation (MPD= (40000×Pore volume)/Surface area). However, above a pore diameter of about 200 A, the measurement of pore volume by nitrogen adsorption becomes less accurate; measurement of a water pore volume by titration of a dry sample until the onset of agglomeration will give a more accurate result.

For some media, the nitrogen adsorption method is unsuitable, for example, non-crosslinked agarose supports which could not withstand the drying step required for the nitrogen adsorption measurements. In this case, size exclusion chromatography can be used to estimate the mean pore diameter. Size exclusion chromatography is a well-known technique in which polymer standards are used to estimate the pore size. Very large polymers cannot enter any of the pores and are excluded, while very small molecules can enter all pores and are totally included. Between these extremes, polymers of intermediate size can enter a fraction of the pore volume and this fraction can be measured and expressed as Kd. Kd for excluded polymers is zero, and for totally included polymers is 1.

A standard system applicable to silicas involves chromatography of polystyrene standards with tetrahydrofuran as solvent. In this system, a polystyrene of molecular weight of about 34000 (log 10 MW=4.5) would have the following approximate Kd values for the following silicas, 60A<0.05; 200A 0.2–0.3; 500A 0.55–0.65; 1000A 0.75–0.85. Thus, silicas of pore size 1000A or less would have a Kd value of less than 0.85 for a polystyrene of molecular weight of 34K daltons. It should be noted that because the Kd value is a function of the log of the molecular weight, small changes in the molecular weight of the 34K standard (ie. variation between 30K and 40K) would have little effect on the result.

Certain media cannot be used in tetrahydrofuran and in these cases a derivatised silica column can be calibrated against polystyrene and then used to calibrate the alternative media. For example, if a carbohydrate type support is to be evaluated, tetrahydrofuran would lead to dehydration but protein standards in aqueous buffer could be accommodated. In this case, a silica of appropriate pore size can be modified with diol groups by well known procedures, and this media calibrated with the polystyrene system. The solvent system can then be changed to one appropriate for protein separation eg. phosphate buffered saline, and a range of protein standards run. This allows the polystyrene calibration to be converted to a protein calibration. The protein standards are then run on the alternative test media and the relevant Kd values compared with the diol media. Such data will only be valid if no adsorption takes place on the column. Tests for adsorption and means of overcoming these by suitable modification of the solvent are well-known to those skilled in the art of gel permeation chromatography.

Immobilisation

There are many known protocols for immobilising proteins or polypeptides on chromatography media. Some of these may be used for immobilising single or multiple variable domain proteins. For example, diol silica may be activated by tresyl chloride and then coupled to a variable domain protein. Alternatively, epoxy-activated silica may be coated with a polymer such as polyethyleneimine (PEI) and the variable domain protein linked to the polymer coat by a bifunctional reagent such as glutaraldehyde.

Procedures for linking proteins to other chromatography media based on agarose, polystyrene, control-pore glass and kieselguhr are also well established in the literature.

Although in practice we have found that a small specific-binding entity, such as an Fv, can sometimes be immobilised directly onto a solid phase without significant loss of activity, in some instances this may not be possible. An additional objective of the present invention is to facilitate the linking of such small specific binding entities to solid phases with even less risk of damage to their essential specific binding properties.

In another embodiment, the invention provides an immunoadsorbent material comprising a specific binding agent immobilised on a solid phase carrier material, wherein the specific binding agent comprises:

i) one or more variable domain proteins (VH and/or VL) unassociated with any substantial portion of originating antibody or antibodies; and ii) a chemical group, preferably a peptide group, (hereinafter referred to as a linking group) which does not contribute to the essential specific binding properties but which can be coupled by chemical or other means to a solid phase carrier material without the essential specific binding activity of the agent being significantly affected. Preferably, the linking group comprises at least 5 amino acid residues. Preferably, the linking group does not comprise more than 20 amino acid residues.

An important embodiment of the invention is a single variable domain protein (Dab) attached to a proteinaceous 'tail' which acts as the linking group as defined above, the 'tail' being coupled to a chromatography medium having a pore size in the range 30–300A, preferably 60–300A without significant loss of specific binding activity.

The properties of the linking group can be chosen to suit the method of attachment most appropriate for the surface to be used. The linking group may be hydrophobic, hydrophilic or of mixed character. It can include potential sites for covalent linkage. Preferably, such a proteinaceous linking group will contain at least one, and more preferably a plurality, of amino acid residues, preferably cysteine, incorporating sulphydryl groups. Sulphydryl groups can act as chemical coupling agents for covalent attachment to chromatography media. This may be done using a bispecific reagent such as succinimidyl - maleimidophenylbutyrate (SMPB). Alternatively, or in addition, the proteinaceous linking group contains at least one, and more preferably a plurality, of lysine residues which possess e-amino groups. The actual coupling can be achieved, for example, by means of conventional bifunctional chemical cross-linking agents. Preferably, such a chemical coupling agent is located at a site sufficiently remote from the variable domain sequence itself that any carrier which becomes coupled to the linking portion is held at a distance from the variable domain sequence. Indeed, the linking group can easily be designed so that the site of coupling orientates the specific binding region in an advantageous position remote from the carrier.

A further important embodiment of the invention is a variable domain provided with a hydrophobic 'tail' which enables the variable domain to be immobilised by non-covalent attachment onto a hydrophobic surface, eg. porous plastics material, such as porous polystyrene. Silica derivatised with standard hydrophobic ligands, such as alkyl chains (eg. $C_8$ or $C_{18}$) or phenyl groups, can easily take up hydrophobic tails of this type.

To provide a linking group with sufficient hydrophobicity to achieve the purposes of the invention, the polypeptide chain comprising the linking group should contain a sufficient number (which may be as few as two, if the residues are adjacent) of amino acid residues selected from the group consisting of valine, leucine, iso-leucine, phenylalanine, tyrosine, tryptophan, proline and alanine. We have found that even if the majority of the amino acid residues in the polypeptide are other, relatively polar (and hence relatively hydrophilic), amino acid residues, the presence of merely a low proportion of residues from the above group can confer effective hydrophobicity on the polypeptide. The hydrophobic region or regions can be adjacent to regions of high charge density, ie. the peptide claim is of mixed character, without the essential hydrophobicity of the linking group as a whole being lost.

A particularly preferred linking group comprises the "Myc" amino acid sequence:

GLU-GLN-LYS-LEU-ILE-SER-GLU-GLU-ASP-LEU-ASN (SEQ ID NO:1)

Since this group contains a lysine residue, it can also be used for covalent attachment onto surfaces.

The linking group will normally be attached at or near one end of a variable domain protein. Normally, the point of attachment will be the amino terminus of the peptide linking group. This is the left hand end of the sequences A and B as seen in FIG. 2 of the accompanying drawings. Preferably, the variable domain protein(s) and the linking group have been produced together by expression in a genetically modified organism. The polypeptide linking group may, for example, be synthesised (cloned) together with a variable domain protein and comprise a proteinaceous tail on one end of the domain sequence. The linking group will comprise at least about 5 amino acid residues, to confer sufficient length to "distance" the variable domain from the surface or tracer to which it is linked.

If desired, a variable domain can be provided with a "natural" hydrophobic polypeptide tail eg. the transmembrane sequence from influenza virus. A phospholipid tail would be an alternative.

The invention also encompasses specific binding reagents composed of a plurality of variable domain proteins. These can be equivalent to natural FV fragments, ie. a heavy chain variable region with a light chain variable protein, or they can comprise combinations of heavy chain or light chain variable region proteins. Such combinations are normally held together by relatively weak interactions. A linking group of the invention can be incorporated at or near one end of one of the variable region protein sequences, but more than one linking group, of the same or differing character, can be incorporated in the combination if desired. The individual variable domain proteins can be expressed separately during cloning. Generally they will combine naturally under mild conditions, which do not inhibit the weak interactions that can cause them to associate.

Advantages of the invention

Immunoaffinity purification is a technique which is extensively used as a research tool but has rarely been used in industrial-scale processes. The novel affinity media of the invention, with single or multiple variable domains as the biospecific ligand, will be more amenable to use in industrial-scale processes by virtue of the following advantages.

i) Reduced molecular weight of ligand

Single variable domain proteins (Dabs) typically have a molecular weight of about 12,000, and Fv fragments about 25,000, compared with approximately 150,000 for an intact antibody. The small proteins may be more easily accommodated in the small pores of rigid chromatography media such as silica. The use of rigid media facilitates scale-up from the laboratory bench to industrial plant. Chromatography silicas which are manufactured for protein purification typically have pores in the range 200A to 300A. Single variable domains and Fv fragments can fit easily into such pores and free exchange of most antigens can still occur without steric hindrance. However, if the antigen is very large (such as a protein in excess of 150 kD) it may be advisable to use a silica of up to 500A pore-size to be sure of allowing free antigen exchange. If the antigen is very small (such as a peptide or non-proteinaceous pharmaceutical product) it may be advisable to use silica with pores in the 30–200A range. This would take advantage of the larger surface area of small-pore silica so that more immunoligand could be immobilised with a resulting increase in capacity per unit volume. Whatever the size of the target analyte, the use of a smaller immunoligand (a Dab or Fv in preference to a whole antibody) will allow a correspondingly smaller silica pore-size to be used. Small-pore silicas typically have the advantages of increased rigidity and a higher surface area.

ii) Reduced affinity of ligand

Some single or multiple variable domains have been found to have reduced affinity for antigen, compared with intact antibody. This may be used to advantage, enabling antigen to be desorbed from the affinity medium under milder conditions, eg. by the use of less harsh buffers than are typically required. This will have the two desirable effects of increasing column lifetime, and reducing risk of inactivating the target analyte (ie. antigen).

iii) Reduced cost of producing ligand

Single or multiple variable domain fragments may be produced at a lower unit cost (ie. cost per binding site) than intact antibody for two reasons. First, there are expression systems available for expressing such fragments in bacteria. Since bacterial culture medium is cheaper than mammalian cell culture medium (typically used for production of intact antibodies by hybridoma cells) considerable savings may be made here. Secondly, since protein synthesis is very costly in terms of cell metabolism, a considerable advantage will be gained by the cell only making proteinaceous structures required for immunodsorption (ie. binding domains) rather than whole antibodies.

Since Dabs and Fvs, produced by genetic engineering, should be cheaper to produce per binding-site than whole antibodies, immunoaffinity purification may now be used cost-effectively on a wider spectrum of target analytes. It is therefore economic to purify lower-value and/or smaller analytes than has been the practise hitherto.

iv) Reduced 'HAMA' response

In immunoaffinity purification, small amounts of the ligand have been shown to leak from the column during operation and appear as contaminant in the preparation of target analyte. If the target analyte is an injectible therapeutic, this can be serious as a souse antibody contaminant may produce an anti-mouse response in the patient— the so-called 'HAMA' response. It has been shown that the HAMA response is primarily directed against the Fc region of the mouse antibody and that variable domain fragments produce a diminished HAMA response. Therefore, any contaminating variable domain fragments in injectibles will be less serious than whole mouse antibody contaminants.

v) Reduced non-specific binding

It is desirable that there should be few, or indeed zero, potential sites for non-specific adsorption present on the immunoligand. By reducing the size of the immunoligand down to the minimum required for specific binding (ie. immobilising the binding domain only) specific binding will be maximised and non-specific binding minimised.

An immunoadsorbent material comprising a porous silica having a pore size in the range 30 to 300A, preferably 60 to 300A, loaded with a specific binding agent which is either a single variable domain (Dab) or an Fv fragment, therefore represents a very advantageous material. The silica carrier material can be manufactured relatively cheaply, and the resulting immunoadsorbent material is physically very robust and can be used in a wide variety of commercial scale immunoadsorption facilities.

The novel immunoadsorbent materials of the invention can be used to extract compounds containing a specific antigen from feedstocks such as fermentation broths, serum, milk whey, and blood.

Production of antibody fragments

The invention is not concerned in principle with novel ways of producing single domain antibody fragments, Fv fragments, or novel ways of producing combinations of such fragments with peptide tails. Fv and single domain fragments can be produced by classical enzyme digestion of intact conventional antibodies. See Hochman et al, *Biochemistry,* (1973) Vol. 12, pages 1130–1135. More preferably, they are produced by genetic engineering, for example as described in Riechmann et al, *J. Mol. Biol,* (1988), Vol. 203, pages 825–828; Skerra et al, *Science,* (1988), Vol. 240, pages 1038–1040; and Ward et al (1989, supra). Ward et al (1989) disclose the production of an anti-lysozyme single domain antibody fragment having a "Myc" tail. This combination could be used in accordance with the present invention, but Ward et al only contemplate the use of the "Myc" tail as an epitope to assist them in their experimental identification and isolation of the anti-lysozyme Dab that they produced. Ward et al make no suggestion that the "Myc" tail might be ideal for immobilising the Dab on porous chromatographic media. As seen below, the procedure of Ward et al can readily be adapted to produce other "tails" on Dab fragments.

A method for the production of a variable domain fragment, and some illustrations of immunoadsorbent materials in accordance with the invention, are given below purely by way of example.

DRAWINGS

The accompanying drawings show:

FIG. 1: Three oligonucleotides useful in the preparation of single domain antibody reagents having linking groups.

FIGS. 2A and 2B: Two linking group peptide sequences that can be produced by means of the oligonucleotides depicted in FIG. 1.

Figure 5:
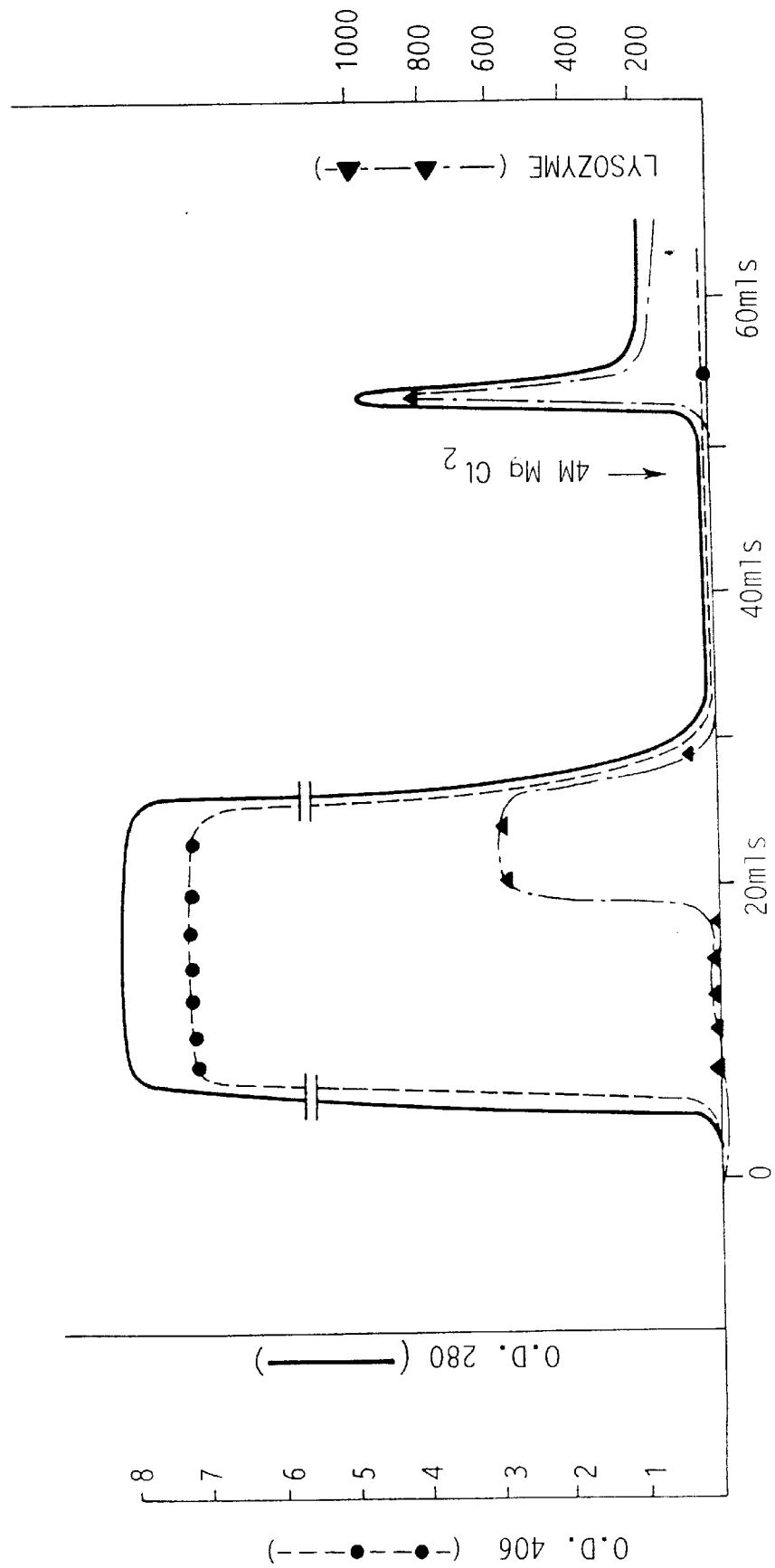

FIG. 5: SDS-PAGE results obtained in Examples 2c and 2d.

Figure 6A:
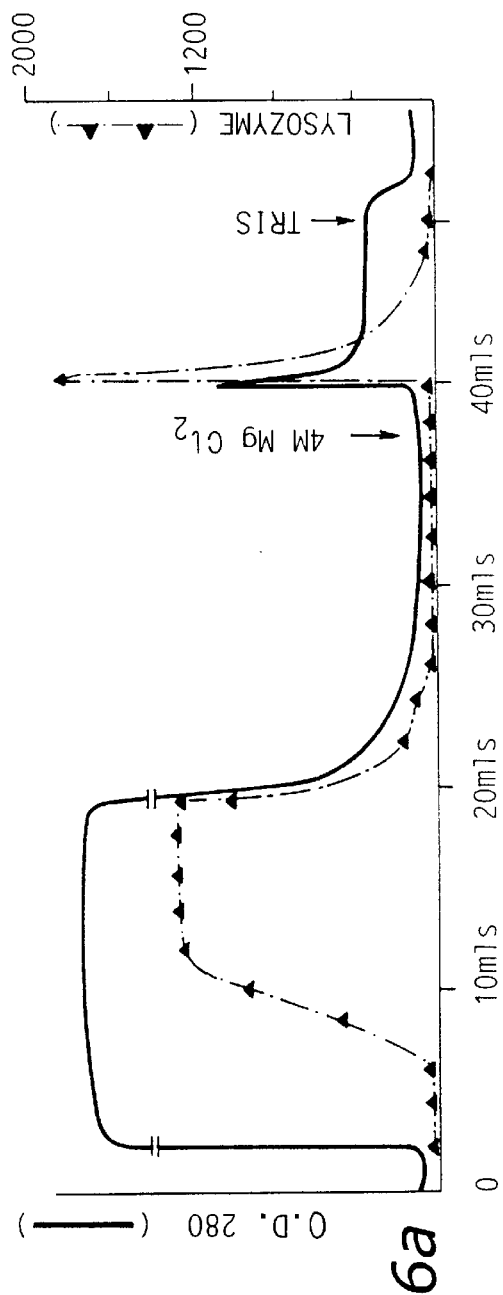
Figure 6B:
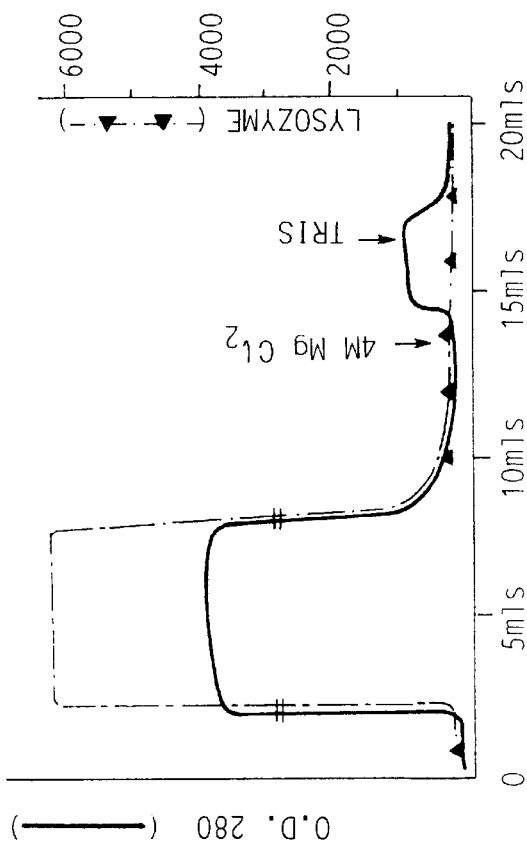

FIG. 6: Chromatograph profile obtained in Example 3.

Figure 7:
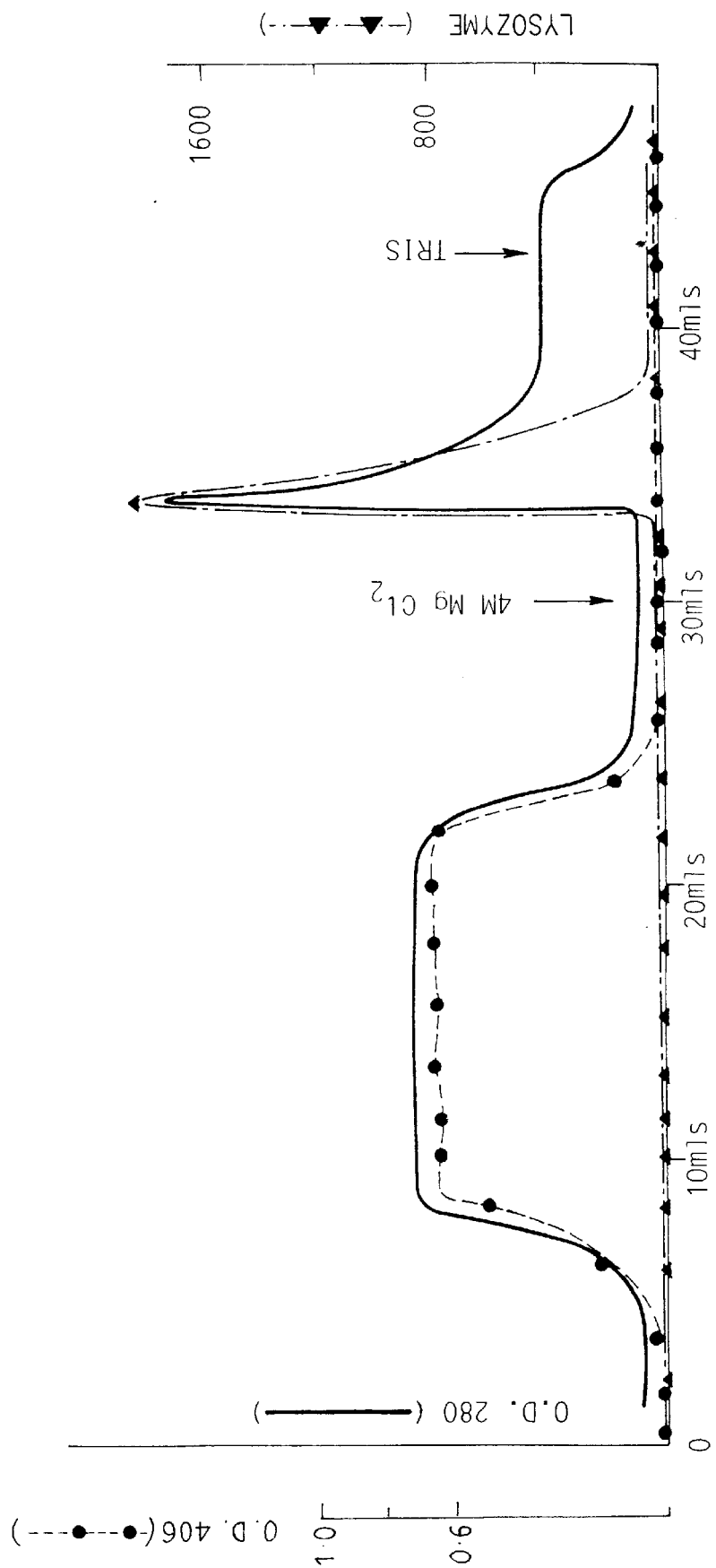

FIG. 7a is a chromatograph profile obtained in Example 4b.

FIG. 7b is a chromatograph profile obtained in Example 4b.

FIG. 8: Chromatograph profile obtained in Example 5.

EXAMPLE 1 a) Preparation of a vector containing the anti-lysozyme $V_H$ fragment D1.3 as a Pst1-BstEII cassette.

The anti-lysozyme $V_H$ fragment D1.3 is excised as a Pst1-BstEII fragment from the expression vector pSW1-VHD1.3-VKD1.3. This vector, and the other expression vector used in this example, pSW1-VHPOLY-TAG1, are described by Ward et al (1989).

pSW1-VHPOLY-TAG1 is restricted with Pst1 and BstEII, and the anti-lysozyme Pst1-BstEII $V_H$ fragment of D1.3 is ligated into the opened vector. This ligation creates an expression vector with the $V_H$ D1.3 fragment inserted and is essentially the same as the expression vector pSW1-VHD1.3-TAG1 (Ward et al.) but with the Pst1 and BstEII restriction sites incorporated. We can refer to this expression vector as pVHD1.3-TAG1.

b) Cloning of a linking group sequence downstream of the cloned $V_H$ gene in pVHD1.3-TAG1.

The replacement of TAG1 by a linking group sequence downstream of the $V_H$ gene is done by the technique of site directed mutagenesis with large oligonucleotides as described in Verhoeyen et al., Science (1988), 239, pages 1534–1536.

Single stranded DNA template is prepared from amp19VHD1.3-TAG1. This is the HindIII-EcoRI fragment from pVHD1.3-TAG1, containing $V_H$ D1.3 and TAG1, cloned in the HindIII and EcoRI sites of mp19. Single stranded DNA obtained from this clone contains the coding strand of the $V_H$ D1.3-TAG1 sequence. A DNA oligonucleotide is hybridized to the template to serve as primer to polyerize a second DNA strand. This oligonucleotide contains the required linking group sequence flanked on either side by 12 bases homologous to the site of integration. The double stranded molecule is transformed in E. coli, where a certain proportion of the molecules is 'repaired' by incorporation of the activation sequence structure. The 12 flanking bases, homologous to the site of integration, are the last four codons of $V_H$ D1.3 and the two stop codons followed by six bases present in pVHD1.3-TAG1. The oligonucleotide replaces the TAG1 gene sequence with that of the linking group gene sequence.

The linking group can be of a hydrophylic, hydrophobic or mixed nature. Convenient restriction sites can be incorporated to facilitate manipulation of the DNA sequences.

FIG. 1 of the accompanying drawings shows three oligonucleotide sequences I, II and III useful in the above procedure. Sequences I and II are alternative sequences for producing an identical hydrophylic linking group, and III can be used to produce a hydrophobic linking group.

FIG. 2 shows the cDNA and amino acid sequences of two linking groups A and B. Linking group A is hydrophilic, and can be produced using either of oligonucleotides I and II. Linking group B is hydrophobic, and can be produced using oligonucleotides III.

Three plasmids derived in this manner, in which the linking group sequence structure contains 12 or 11 amino acids (n=1), and designated pVHD1.3-ADI, pVHD1.3-ADII and pVHD1.3-ADIII, are produced using sequences I, II and III. These plasmids are expressed in E. coli (as in Ward et al.).

The $V_H$ fragments are checked for activity by ELISA, and for purity by SDS-PAGE.

$V_H$ and $V_L$ fragments, with and without "tails", and also Fv fragments, can be prepared readily using similar procedures following the teaching in the publications cited earlier.

EXAMPLE 2

Figure 3A:
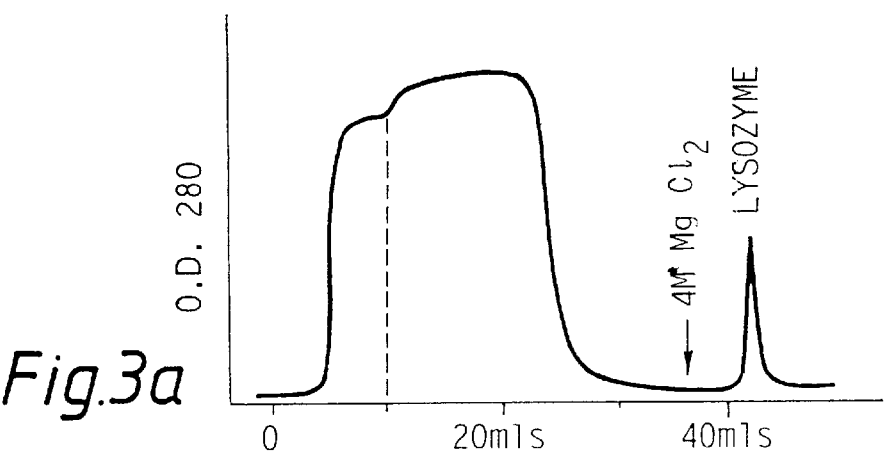
FIG. 3a is a chromatograph profile obtained in Example 2b.

Immobilisation of an anti-lysozyme Fv on agarose and its use as an immunoadsorbent a) Preparation of immunoadsorbent 2 mgs of anti-lysozyme Fv (with no linking group) at a concentration of approximately 400 μg/ml was dialysed against coupling buffer (0.1M NaHCO$_3$+0.5MNaCl pH8.3). Small-bore dialysis tubing was used (Spectrum 132580). CNBr-activated Sepharose 4B (Pharmacia 17-0430-02) was swollen and washed in 1 mM HCl. 3 mls of swollen gel was added to the Fv preparation in a stoppered vessel. The mixture was gently rotated overnight at 4° C. The Sepharose was recovered by centrifugation and blocked by rotating overnight at 4° C. with 1M ethanolamine made up in coupling buffer. The immunoadsorbent was washed three times in Tris buffer (0.1M Tris pH8+0.1% azide) and packed in a glass column (Pharmacia 19-5002-01).

b) Recovery of lysozyme from a 10-fold excess of albumin 2 mgs of hen-egg lysozyme (Sigma L-6876) and 20 mgs of bovine albumin (Sigma A-7888) were made up in 20 mls of Tris buffer. This feedstock was loaded onto the immunoadsorbent which was then washed with Tris buffer. Bound protein was eluted with 4M MgCl$_2$ made up in Tris buffer. The capacity of the immunoadsorbent was calculated by determining the point of breakthrough for lysozyme. It was found to be 0.5 mgs (see FIG. 3a). The extent of non-specific binding was determined by two control experiments:

Control experiment 1

20 mgs of bovine albumin was made up in 20 mls of Tris buffer and applied to the immunoadsorbent. The immunoadsorbent was washed with Tris buffer; bound material was eluted with 4M MgCl$_2$ made up in Tris buffer.

Control experiment 2

A 'blank' column was made by blocking 3 mls of swollen CNBr-activated Sepharose with 1M ethanolamine made up in coupling buffer. The Fv immunoligand was not added. 20 mgs of lysozyme was made up in 20 mls of Tris buffer and applied to the column. The column was washed with Tris buffer; bound material was eluted with 4M MgCl$_2$ made up in Tris buffer.

Figure 3B:
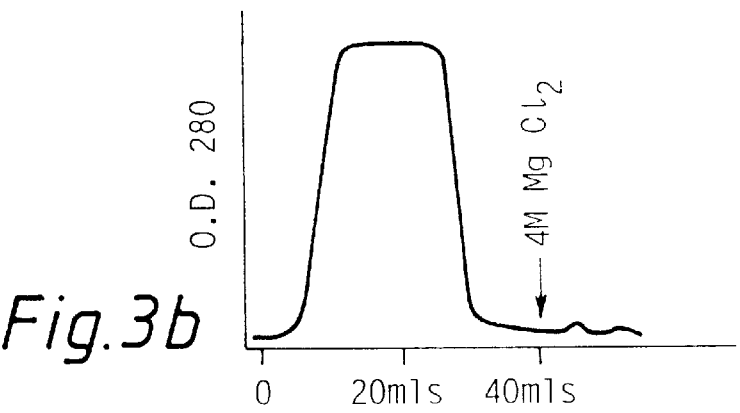
FIG. 3b is a chromatograph profile obtained in control experiment 1, Example 2b.
Figure 3C:
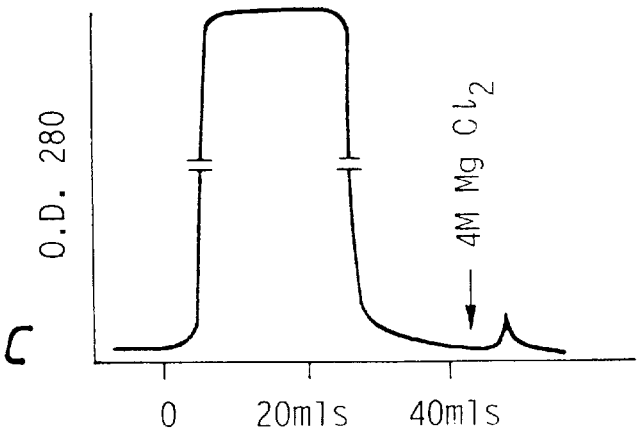
FIG. 3c is a chromatograph profile obtained in control experiment 2, Example 2b.
Figure 4A:
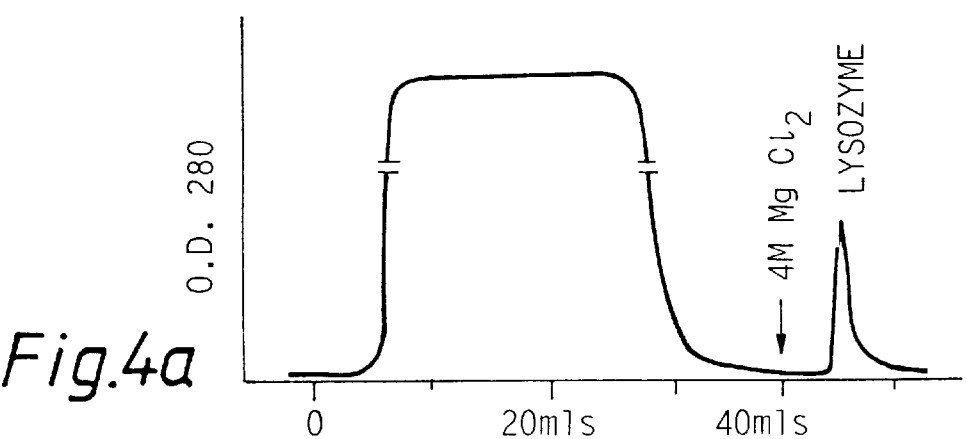
FIG. 4a is a chromatograph profile obtained in Example 2c.

In both control experiments non-specific binding was minimal (see FIGS. 3b and 3c respectively).

c) Recovery of lysozyme from 5% horse serum 1 mls of horse serum (Seralab S-0004a) was made up to 20 mls (ie. 5% serum) in Tris/Tween buffer (0.1M Tris pH8, 0.1% azide, 0.15% Tween 20 - Sigma P1379). This feedstock was spiked with 2 mgs of hen-egg lysozyme and passed through a 0.45 μm filter (Schleicher and Schuell 452100). 20 mls of spiked serum ('feedstock A') was loaded onto the immunoadsorbent which was then washed with Tris/Tween buffer. Bound material was eluted with 4M MgCl$_2$ made up in Tris buffer. The eluted fraction was found to be homogeneous lysozyme by analysis with SDS-PAGE after dialysing against Tris buffer. The system used was a pre-poured gel (Pharmacia 17-0624-01) together with SDS buffer strips (Pharmacia 17-0516-01). The gel was stained with silver-stain. The chromatograph is shown in FIG. 4a and the electrophoretic gel in FIG. 5. The loading of samples on the gel was as follows:

| | |
|---|---|
| Lane 3 | Feedstock A |
| Lane 4 | Lysozyme recovered from feedstock A |
| Lane 5 | Lysozyme standard |
| Lane 6 | Molecular weight markers |

The extent of non-specific binding was determined by two control experiments.

Control experiment 1

20 mls of unspiked serum (ie. no lysozyme added) was prepared as before. The unspiked serum was loaded onto the immunoadsorbent in Tris/Tween buffer and washing/elution conditions were repeated as before.

Control experiment 2

10 mls of spiked serum was loaded onto the 'blank' column (described in Example 3b) in Tris/Tween buffer and elution conditions were repeated as before.

Figure 4B:
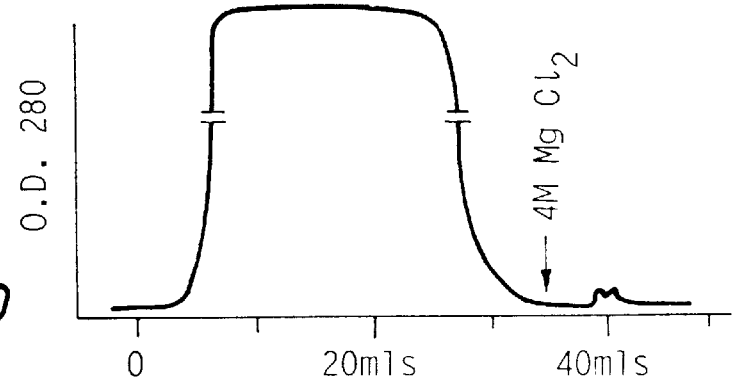
FIG. 4b is a chromatograph profile obtained in control experiment 1, Example 2c.
Figure 4C:
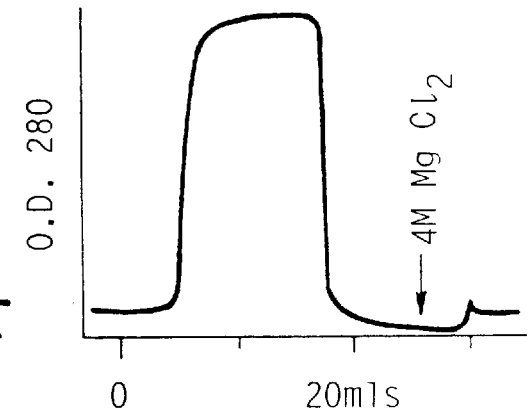
FIG. 4c is a chromatograph profile obtained in control experiment 2, Example 2c.

In both control experiments non-specific binding was minimal (see FIGS. 4b and 4c respectively).

d) Recovery of lysozyme from a mixture of proteins 4 mgs of each of the following proteins were added together, made up to 30 mls in Tris/Tween buffer and passed through an 0.45 μm microfilter:

Bovine albumin (Sigma A-7888), Myoglobin (Sigma), Haemoglobin (an in-house preparation), Trypsin (Sigma T-8003), Lysozyme (Sigma L-6876), Transferrin (Sigma), Cytochromec (Sigma C-7752) and Ovalbumin (Sigma).

This protein mixture ('feedstock B') was loaded onto the immunoadsorbent which was then washed with Tris/Tween buffer. Bound material was eluted with 4M $MgCl_2$ made up in Tris buffer. The eluted fraction was found to be homogeneous lysozyme by analysis with SDS-PAGE after dialysing against Tris buffer (FIG. 5).

The loading of samples on the gel was as follows:

| | |
|---|---|
| Lane 1 | Feedstock B |
| Lane 2 | Lysozyme recovered from feedstock B |
| Lane 5 | Lysozyme standard |
| Lane 6 | Molecular weight markers. |

EXAMPLE 3

Immobilisation of an anti-lysozyme Fv on porous silica and its use as an immunoadsorbent a) Preparation of immunoadsorbent 6 mgs of anti-lysozyme Fv (with TAG1, ie. the "Myc" tail, as a linking group) at a concentration of approximately 240 $\mu$g/ml was dialysed against phosphate buffer (0.1M $NaH_2PO_4$ pH7). The dialysis tubing was Spectrum (132580). Glutaraldehyde-activated silica with approximately 200A pore-size (PREPSCALE Glutaraldehyde-P, J T Baker 7567-02) was washed in phosphate buffer. 3.5 mls of washed silica was added to the Fv preparation in a stoppered vessel. The mixture was slowly rotated, and sodium cyanoborohydride was added at 4° C. in aliquots over a period of 5 hours to reach a final concentration of 0.1M, and the mixture tumbled overnight at 4° C. The product (immunoadsorbent) was washed with phosphate buffer, followed by phosphate buffer containing 1M sodium chloride. The immunoadsorbent was then washed and blocked with 0.2M pH7 ethanolamine overnight at 4° C. The immunoadsorbent was equilibrated in Tris buffer and packed in a glass column (Pharmacia 19-5002-01).

b) Recovery of lysozyme from a 25-fold excess of Cytochrome c

A mixture of two proteins was made up to the following specifications in Tris buffer:- hen-egg lysozyme (Sigma L-6876) @ 0.04 mg/ml and cytochrome c (Sigma C-7752) @ 1 mg/ml. 20 mls of this mixture was loaded onto the immunoadsorbent which was then washed with Tris buffer. Bound material was eluted with 4M $MgCl_2$ made up in Tris buffer. The eluted fraction was dialysed against Tris buffer using Spectrum dialysis tubing (132580). A chromatograph profile was generated using an on-line spectrophotometer (LKB "UVICORD") set at 280 nm to detect both proteins.

The fate of lysozyme and Cytochrome c was determined by making specific measurements for these two proteins across the chromatograph profile (FIG. 6). Lysozyme was determined by measuring enzyme activity using a suspension of Micrococcus (Sigma M-3770). 2.5 ml of *Micrococcus lysodelkticus* suspension, containing 1.5 mg of M-3770 in 10 ml of 0.066M potassium phosphate buffer, pH6.24 at 25° C., was pipetted into a quartz cuvette (1 cm light path). The absorbance at 450 nm of this suspension was between 0.6 and 0.7, measured using a LKB "ULTRASPEC" photometer. Lysozyme solution was added, and the decrease in absorbance at 450 nm monitored to obtain the change/minute using the maximum linear rate, and compared with a known lysozyme standard to determine the amount in Enzyme Units per ml. Cytochrome c was determined by measuring the optical density at 406 nm, the absorbance maximum for this protein.

It was found that the separation of lysozyme from Cytochrome c was total and that the breakthrough for lysozyme was sharp (FIG. 6). Since Cytochrome c and lysozyme are physically very similar (cytochrome c:- M.W.=12,300, pI=10.5; lysozyme:- M.W.=14,500, pI=11.0) their complete separation represents a high resolution event.

EXAMPLE 3c

Immunoelectron microscopy of immuoadsorbent to show distribution of bound lysozyme The immunoadsorbent described above was removed from the column. The immunoadsorbent was placed in a 1 mg/ml solution of lysozyme in Tris buffer. Excess lysozyme was removed by washing with Tris. Silica particles were fixed using 1% paraformaldehyde plus 0.05% glutaraldehyde in phosphate buffered saline for 2 hours at 4° C.; then embedded in resin. Ultrathin sections (approximately 90 nm thick) were prepared on nickel grids.

Grids and sections were blocked with 1% ovalbumin plus 5% goat serum in phosphate buffered saline; then left overnight in a solution of rabbit anti-lysozyme antibody made up in 1% ovalbumin, 5% goat serum, 0.1% Tween 20 in phosphate buffered saline. Grids were then washed with phosphate buffered saline and incubated with goat anti-rabbit antibody conjugated to 5 nm colloidal gold (Biocell).

Election microscopy showed the lysozyme to be evenly distributed throughout the silica particles. A negative control where the rabbit anti-lysozyme antibody was omitted proved to be blank. The enzyme was uniformly dispersed throughout the porous structure of the silica support, indicating that the Fv was located over the whole surface within the pores and that the enzyme had also become bound within the pores.

EXAMPLE 4

Recovery of lysozyme from serum using an FV-fragment immobilised on silica a) Preparation of immunoadsorbent Epoxy silica particles with pore-size of approximately 200A (C200, Crosfield Chemicals) were converted to the diol derivative by the method of Mohan et al (In Separations for Biotechnology ed D L Pyle, 1990). C200 Diol particles were tresylated as follows:

2 g of diol silica was stirred gently in 100 mls of dry acetone (BDH) containing 0.76 mls of dry triethylamine (Fluka) and 0.666 g of 4-dimethylaminopyridine (Fluka). 50 mls of a 2% solution of tresyl chloride (Fluka) made up in dry acetone was slowly dripped into the gently stirring silica over a period of two hours (keeping the temperature below 30° C.). After a further hour, the contents were washed into a filter funnel and paper (Whatman No. 1) using ethanol (BDH). Further washing with ethanol was undertaken (5×30 mls), followed by washing with a 1:1 ethanol/acetone mix (5×30 mls) and finally washing with acetone only (5×30 mls). The silica was then dried in a forced air (fan) oven overnight at 30° C.

0.9 g of tresylated C200 was washed with 10 mls of 1M NaCl and then 100 mls of borate buffer (0.1M $Na_2 B_4 O_7$/HCl, pH 8.5). The silica was then added to 14 mls of a solution of anti-lysozyme Fv (with no linking group) and rotated overnight at 4° C. in a stoppered vessel. The Fv solution was approximately 350 $\mu$g/ml in PBS (0.01M sodium phosphate, 0.15M NaCl, pH7). The immunoadsorbent was recovered by centrifugation, approximately 1 mg of Fv protein was found to have been coupled by analysis with the BCA protein assay (Pierce). The immunoadsorbent was blocked by rotating overnight in 1M ethanolamine made up in borate buffer. The immunoadsorbent was then washed three times in Tris buffer and packed in a glass column.

b) Recovery of lysozyme from 10% horse serum 20 mls of 10% horse serum (diluted in Tris buffer) was spiked with hen-egg lysozyme to a final concentration of 0.02 mg/ml. The spiked serum was passed through a 0.45 µm filter and loaded onto the immunoadsorbent, and eluted and analysed as in Example 3b. The eluted peak was found to be highly enriched for lysozyme (FIG. 7a).

To determine the extent of non-specific binding, a 'blank' column was made by blocking 0.2 g of tresylated C200 with 1M ethanolamine made up in borate buffer. The Fv immunoligand was not added. 5 mls of 10% horse serum was spiked with hen-egg lysozyme to a final concentration of 0.1 mg/ml and applied to the blank column. The column was washed and eluted as before. Neither the lysozyme nor the serum bound to the column (FIG. 7b).

This demonstrates that the recovery of lysozyme is by virtue of specific interaction with the Fv immunoligand.

EXAMPLE 5

Immobilisation of an anti-lysozyme Dab on porous silica and its use as an immunoadsorbent a) Preparation of immunoadsorbent 1 g of glutaraldehyde-activated silica with approximately 200A pore-size (PREPSCALE Glutaraldehyde-P, J T Baker 7567-02) was washed as in Example 3a. The washed silica was added to 10 mls of a Dab preparation. The Dab was an anti-lysozyme $V_H$ with the "myc" peptide as a linking group. The concentration of protein was approximately 70 µg/ml in PBS (0.01M sodium phosphate, 0.15M NaCl, pH7). Coupling was perfomed as in Example 3a.

b) Recovery of lysozyme from a 10-fold excess of cytochrome c

A mixture of two proteins was made up to the following specifications in Tris/Tween buffer (0.1M Tris, pH8, 0.15% Tween):- hen-egg lysozyme @ 0.01 mg/ml and cytochrome c @ 0.1 mg/ml. 20 mls of this mixture was loaded onto the immunoadsorbent, and eluted and analysed as in Example 3b. The fate of lysozyme and cytochrome c was determined as described in Example 3.

It was found that the separation of lysozyme from cytochrome c was total (FIG. 8). Since cytochrome c and lysozyme have very similar molecular weights and isoelectric points, their complete separation represents a high resolution event.

We claim:

1. An immunoadsorbent material consisting essentially of a specific binding agent having a molecular weight of not more than about 25,000 and composed of one or more variable domain antibody proteins (VH and/or VL; where corresponding VH and VL are held together solely by hydrophobic interactions), immobilized on a porous solid phase carrier material having a nominal pore size of less than 1000A, said binding agent as immobilized maintaining its specific binding activity.

2. An immunoadsorbent material according to claim 1, wherein said specific binding agent is a natural Fv.

3. An immunoadsorbent material according to claim 1 or 2 wherein said carrier material has a nominal pore size of less than about 500A, but at least about 30A.

4. An immunoadsorbent material according to claim 1 or 2, wherein said carrier material has a nominal pore size of less than about 300A but at least about 60A.

5. An immunoadsorbent material according to claim 1 or 2, wherein said carrier material is selected from the group consisting of porous amorphous silica or controlled-pore glass.

6. An immunoadsorbent material consisting essentially of a specific binding agent immobilized on a porous solid phase carrier material, wherein said specific binding agent is composed of:
   i) one or more variable domain antibody proteins (VH and/or VL; where corresponding VH and VL are held together solely by hydrophobic interactions) unassociated with any other substantial portion of the originating antibody or antibodies; and
   ii) a chemical group, which does not contribute to the essential specific binding properties but which can be coupled by chemical or other means to a solid phase carrier material without the essential specific binding activity of the agent being significantly affected, said porous solid phase carrier material having a nominal pore size of less than about 1000 A.

7. An immunoadsorbent material according to claim 6, wherein said specific binding agent is coupled to said carrier material via a peptide linking group comprising at least 5 amino acid residues but not more than 20 amino acid residues.

8. An immunoadsorbent material according to claim 7, wherein said linking group is hydrophobic.

9. An immunoadsorbent material consisting essentially of natural Fv fragment, immobilized on a porous solid phase carrier material having a nominal pore size of at least about 30A and less than about 500A, said immobilized fragment maintaining its binding activity.

10. An immunoadsorbent material consisting essentially of a single-chain Fv immobilized on a porous solid phase carrier material having a nominal pore size of less than 1000A but at least about 30A, said immobilized Fv maintaining its binding activity.

11. An immunoadsorbent material according to claim 10, wherein said carrier material has a nominal pore size of less than about 300A but at least about 60A.

12. An affinity purification process using an immunoadsorbent material according to claim 1, claim 10 or claim 11.

13. In an affinity purification process using an immunoadsorbent material, the improvement wherein the immunoadsorbent material is one comprising an Fv fragment or Dab, immobilized on a porous carrier material selected from the group consisting of amorphous silica, controlled-pore glass, and synthetic polymers and copolymers, and wherein said carrier material has a nominal pore size in the range 30–300A, said immunoadsorbent material enhancing the speed or throughput of said affinity purification process and said immobilized fragment or Dab maintaining its specific binding activity.

* * * * *